United States Patent [19]

Berényi née Poldermann et al.I70[45]

[11] Patent Number: 4,652,562

[45] Date of Patent: Mar. 24, 1987

[54] QUINOLINE DERIVATIVES AND PHARMACEUTICAL COMPOSITIONS

[75] Inventors: Edit Berényi née Poldermann; László Varga; László Pallos; Lujza Petöcz; László Ladányi; Péter Tömpe; Eva Hartai née Zsorzs; Agnes Kovács née Palotai, all of Budapest, Hungary

[73] Assignee: Egis Gyogyszergyar, Budapest, Hungary

[21] Appl. No.: 870,396

[22] Filed: Jun. 4, 1986

[30] Foreign Application Priority Data

Jun. 4, 1985 [HU] Hungary ............................. 2193/85

[51] Int. Cl.[4] ................... A61K 31/47; A61K 31/535; C07D 413/12
[52] U.S. Cl. .................................... 514/237; 514/222; 514/252; 514/313; 544/58.6; 544/128; 544/363; 546/163
[58] Field of Search ...................... 544/58.6, 128, 363; 546/163; 514/222, 237, 252, 313

[56] References Cited

U.S. PATENT DOCUMENTS 4,293,549 10/1981 Rachlin et al. ...................... 514/313

OTHER PUBLICATIONS

Berenyi et al., Chemical Abstracts, vol. 96, No. 181249p (1982).

Primary Examiner—Robert W. Ramsuer
Attorney, Agent, or Firm—Keil & Weinkauf

[57] ABSTRACT

The invention relates to new quinoline derivatives of the general Formula I

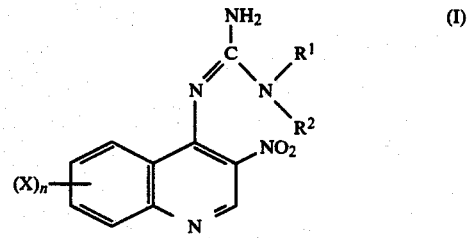

(wherein
X stands for hydrogen, halogen or lower alkoxy;
n is an integer of 1, 2 or 3;
$R^1$ represents hydrogen and
$R^2$ represents hydroxy-lower alkyl or lower alkoxy-lower alkyl or a group of the general formula IV,

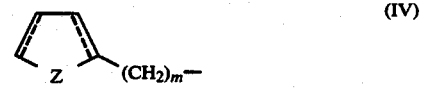

wherein
Z stands for —O—, —S—, —NH— or —N(lower alkyl)—; the dotted lines represent optional bonds; and
m is 0 or 1; or
$R^1$ and $R^2$ together with the adjacent nitrogen atom, they are attached to, form a 5- or 6-membered heterocyclic group which may optionally contain a further oxygen, nitrogen or sulfur heteroatom and may be optionally substituted), and pharmaceutically acceptable acid addition salts thereof. The new compounds of the present invention exhibit radiosensitizing effect, make hypoxial cells highly sensitive towards radiation and may be used in radiation therapy.

6 Claims, No Drawings

QUINOLINE DERIVATIVES AND PHARMACEUTICAL COMPOSITIONS

This invention relates to new quinoline derivatives, a process for the preparation thereof and pharmaceutical compositions comprising the same.

According to an aspect of the present invention there are provided new quinoline derivatives of the general Formula I

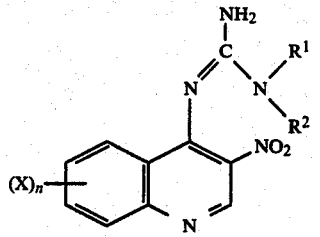

and pharmaceutically acceptable acid additions salts thereof
[wherein
X stands for hydrogen, halogen or lower alkoxy;
n is an integer of 1, 2 or 3;
$R^1$ represents hydrogen and
$R^2$ represents hydroxy-lower alkyl or lower alkoxy-lower alkyl or a group of the general Formula IV,

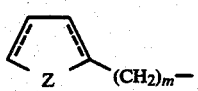

wherein
Z stands for —O—, —S—, —NH— or —N(lower alkyl)—; the dotted lines represent optional bonds; and
m is 0 or 1; or
$R^1$ and $R^2$ together with the adjacent nitrogen atom, they are attached to, form a 5- or 6-membered heterocyclic group which may optionally contain a further oxygen, nitrogen or sulfur heteroatom and may be optionally substituted].

The new compounds of the present invention exhibit radiosensitizing effect, i.e. make hypoxial cells highly sensitive towards radiation.

In prior art there are described some compounds having the above field of activity. Reference is made to the following compounds and publications, respectively: 3-methoxy-1-(2-nitro-1-imidazole-1-yl)-2-propanol of the Formula V

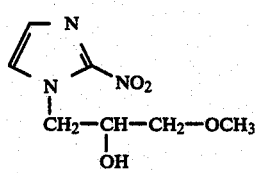

[misonidazole; T. W. Wong, G. F. Withmore and S. Gulyás: Radiat. Res. 75, 541–555 (1978); J. E. Pederson et al.: Dr. J. Cancer 39, 429–433 (1979)]; 1-(2-hydroxyethyl)-2-methyl-5-nitroimidazole of the Formula VI

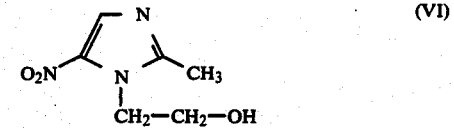

[metronidazol; Adams G. E.: Int. I. Radiat. Biol. Rolat. Stud. Phys. Chem. Med. (1979), 35 (2), 151–60] and tetramethyl-diazene-dicarboxamide of the Formula VII

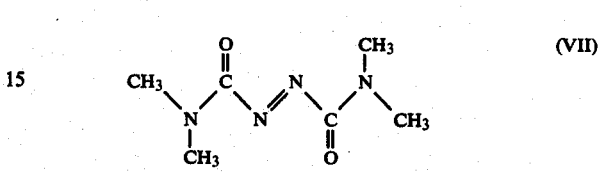

[diamide; J. W. Harris, J. A. Power and C. I. Koch: Radiat Res. 64, 270–280 (1975)].

As shown by comparative test results in the present specification, the new compounds of the general formula I are significantly superior to the above known derivatives.

The term "lower" relates to groups having 1–7, preferably 1–4 carbon atoms. The terms "lower alkoxy" relates to straight or branched chained alkoxy groups having 1–7, preferably 1–4 carbon atoms (e.g. methoxy, ethoxy, isopropoxy, etc.) The term "lower alkyl" relates to straight or branched chained alkyl groups having 1–7, preferably 1–4 carbon atoms (e.g. methyl, ethyl, n-propyl, isobutyl etc.). The term "halogen" encompasses the fluorine, chlorine, bromine and iodine atoms.

Z stands preferably for oxygen.

If $R^1$ and $R^2$ together with the adjacent nitrogen atom, they are attached to, form a 5- or 6-membered heterocyclic group which optionally bears a further oxygen, sulfur or nitrogen heteroatom and may be optionally substituted, the said heterocyclic group may preferably be an optionally substituted morpholino, piperazino, piperidino or pyrrolidino group. The heterocyclic ring may optionally bear one or more identical or different hydroxy, lower alkoxy, lower alkyl, hydroxy-(lower alkyl), lower alkoxycarbonyl and/or nitro substituent(s).

$R^1$ and $R^2$ together with the adjacent nitrogen atom, they are attached to, preferably form a morpholino, piperazino, piperidino, 4-(2-hydroxy-ethyl)-piperazino, 4-hydroxy-piperidino or pyrrolidino group.

X preferably stands for hydrogen.

A particularly preferred representative of the compounds of the general Formula I is the N-(3-nitro-4-quinolyl)-morpholino-carboxamidine and pharmaceutically acceptable acid addition salts thereof.

The pharmaceutically acceptable acid addition salts of the compounds of the general Formula I may be salts formed with pharmaceutically acceptable inorganic acids (e.g. hydrochloric acid, hydrogen bromide, sulfuric acid, phosphoric acid etc.) or organic acids (e.g. glyoxylic acid, maleic acid, fumaric acid, citric acid, lactic acid etc.).

According to a further feature of the present invention there is provided a process for the preparation of compounds of the general Formula I (wherein X, n, $R^1$ and $R^2$ are as stated above) which comprises reacting a quinoline derivative of the general Formula II

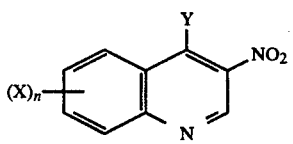

(wherein X and n are as stated above and Y stands for a leaving group) or an acid addition salt thereof with a guanidine derivative of the general Formula III

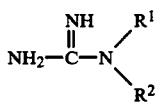

(wherein $R^1$ and $R^2$ are as stated above) or an acid addition salt thereof and, if desired, converting a compound of the general Formula I thus obtained into a pharmaceutically acceptable acid addition salt thereof or setting free a compound of the general Formula I from a salt thereof.

The starting materials of the general Formulae II and III may also be applied in the form of acid addition salts thereof (e.g. as hydrochloride or hemisulfate). If the said starting materials are used in the form of an acid addition salt, the compound of the general Formula II and III, respectively, may be set free from the said salts in the reaction mixture with a base (e.g. an alkali alcoholate such as sodium or potassium methylate or ethylate).

The reaction of the compounds of the general Formula III may be carried out preferably in an inert solvent. As reaction medium preferably an alcohol (e.g. ethanol or methanol); a chlorinated hydrocarbon (e.g. chlorobenzene), a polar aprotic solvent (e.g. dimethyl formamide, dimethyl sulfoxide or dimethyl acetamide) or a mixture thereof may be used.

The reaction may be accomplished at a temperature between 0° C. and 150° C., advantageously at 70°–100° C.

The reaction of the compounds of the general Formulae II and III may be carried out optionally in the presence of an acid binding agent. For this purpose preferably an organic amine (e.g. triethyl amine or pyridine) or an excess of the starting material of the general Formula III may be used.

It is preferred to use starting materials of the general Formula II, wherein Y stands for halogen, preferably chlorine. However, in the starting materials of the general Formula II Y may stand for any suitable leaving group which is split off when reacting with the compound of the general Formula III.

The reaction takes place within a few hours. The compound of the general Formula I may be isolated from the reaction mixture by usual methods. Thus one may proceed by cooling the reaction mixture, separating the compound of the general Formula I by filtration or centrifuging and washing and drying the same.

The compounds of the general Formula I may be converted into the acid addition salts thereof by methods known per se by reacting with the corresponding acid in a suitable solvent.

The starting materials of the general Formulae II and III are known compounds or may be prepared by methods used for the preparation of analogous compounds being known per se [A. R. Surrey, R. A. Cutier: J. Am. Chem. Soc. 73, 2415 (1951); R. D. Fearing, S. W. Fox: J. Am. Chem. Soc. 76, 4382–5 (1955); Org. Synth. Coll. Vol. III. 440 John Wiley and Sons, Inc. (1955)].

The compounds of the general Formula I form tautomeric forms (see general Formulae I and IA).

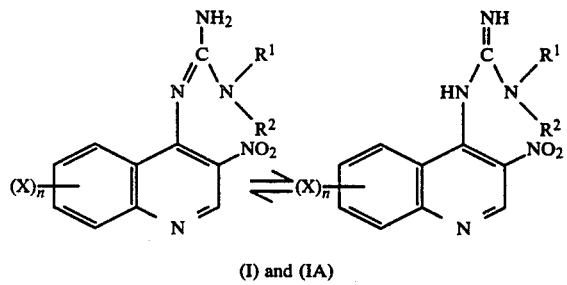

The present invention relates to all tautomeric forms of the compounds of the general Formula I and a process for the preparation thereof and pharmaceutical compositions comprising the same.

The compounds of the general Formula I possess radiosensitizing effect and are capable of making hypoxial cells highly sensitive towards radiation.

The effective treatment of human malignancies is based on the surgical removal, on the administration of chemotherapeutic drugs and on the cell inactivation by ionizing radiation. The application of these modes separately or in combination has led to significant improvement in the tumor therapy, in some cases, however, failed to control the tumors at the local treatment site. The cause of failures might be explained by several factors, among others that tumors with hypoxic cells are more radioresistant than the surrounding normal tissues. To overcome this problem in the radiotherapy, it would be necessary to have radiobiologically more effective, new types of radiating beam. It is generally accepted that the further increase of effective power of the conventional radiation sources is not expected in the near furture, the use of high LET radiations (neutrons, protons, mesons, ions, etc.) is limited by technical difficulties and financial reasons. Therefore, to produce larger therapeutic gain, one possible way could be to change the radiation response of malignant cells to advantageous direction (sensitization), while to protect the normal tissues from radiation damage (radioprotection). To follow this conceptional approaches, intensive research work has been initiated all over the world and reached the nitro-imidazole derivatives within the great family of so-called electronaffinic radiosensitizers. The best representatives of nitro-imidazoles are metronidazole [1-(2-hydroxy-ethyl)-2-methyl-5-nitro-imidazole] and misonidazole [3-methoxy-1-(2-nitro-imidazole-1-yl)-2-propanol].

As is known [T. W. Wong, G. F. Whitmore and S. Gulyas: Radiat. Res. 75, 541–555 (1978)], parameters derived from radiation survival curves can be used for characterization of modifying effect, e.g. the slope of the exponential portion of survival curve and the calculated mean lethal dose ($D_o$) as well as the overall extrapolation number (N).

The dose multiplication radiosensitization (DMR) means the ability of a given compound to increase the slope of the survival curve and consequently to decrease the mean lethal dose ($D_o$).

On the effect of dose-additive radiosensitization (DAR) there is a reduction in the shoulder region of radiation survival curves, and in the best cases the sigmoid type survival curves characteristic of mammalian cells change into exponential ones. This indicates that the cell killing effect of ionizing radiation can be seen only after a given threshold dose of radiation in untreated cultures while pretreatment of cells with drugs having the above-mentioned ability cause lethality after smaller radiation doses.

For the degree of radiation modification, the quasi threshold dose ($D_q$) can be used, as well. This dose represents the width of shoulder region of radiation survival curves ($D_q = D_o$ ln N). The meaning of this measure from radiobiological point of view is the minimal dose necessary to produce appreciable cell killing effect.

The well-known nitro-imidazoles can enhance the radiation sensitivity of hypoxic cells, but almost exclusively by dose-multiplicative radiosensitization.

Further disadvantage of nitro-imidazole derivatives is the severe peripheral neurotoxicity observed during clinical test after giving the necessary effective drug dose, and this circumstance limits very much their application in human therapy.

The new compounds of the general Formula I of the present invention surprisingly do not show at all the disadvantages mentioned above. Beside a relatively low toxicity they possess both dose-multiplicative- and dose-additive-radiosensitization, therefore they might serve beneficially for the combined treatment of human cancers.

The effect of the compounds of the invention can be verified by the following experiments.

1. The toxicity and radiation modifying ability of the compounds of the general Formula I have been compared to misonidazole, one of the most valuable nitro-imidazole derivatives. According to the literature data, studies were undertaken on the same test-systems [Chinese hamster ovary cells cultured in vitro (CHO) and under similar circumstances (oxygenic- and hypoxic conditions, $\alpha$-MEM with 10% foetal calf serum)]. The N-(3-nitro-4-quinoline)-morpholino-carboxamidine, one of the most promising representative of the compounds of the general Formula I, exhibited lower toxicity than that of misonidazole. This compound showed advantageous toxicity in test animals (CFLP mice), too, as is seen in Table I.

TABLE I

| Test compound | LD$_{50}$ per os |
|---|---|
| N—(3-Nitro-4-quinolyl)-morpholino-carboxamidine | >2000 mg/kg |

2. As already mentioned, the well-known nitro-imidazole derivatives exhibit only dose-multiplicative radiosensitization [the slope of the radiation survival curve increases, consequently the mean lethal dose ($D_o$) decreases]. In contrast, the new compounds of the general Formula I show both dose-multiplicative- and dose-additive-radiosensitization; accordingly, the sigmoid (shoulder)-type survival curve characteristic for mammalian cells changes into an exponential one (the value of overall extrapolation number (N) becomes 1).

The above-mentioned effects, though seeming to be very important from radiobiological aspects, can be found only in a small degree after misonidazole treatment (T. W. Wong, G. F. Whitmore and S. Gulyas: Radiat. Res. 75, 541–555 [1978]). Under hypoxic conditions, after several hours incubation, the overall extrapolation number (N) did not fall below 5. In case of an other well-known compound, diamide, either dose-multiplicative- or dose-additive-radiosensitization could be observed at a lower temperature (0° C.) depending on the drug concentration applied, but both effects did not appear simultaneously (J. W. Harris, J. A. Power and C. J. Koch: Radiat. Res. 64, 270–280 [1975]). At higher temperature (37° C.), however, diamide proved to be extremely toxic, therefore its test in animal or human organism could not come in question.

3. Comparing the effectiveness of dose-multiplicative-radiosensitization of the new compounds of the general Formula I over well-known chemical sensitizers, there is also a remarkable advantage, which can be characterized quantitatively by the mean lethal doses.

Experiments were undertaken with hypoxic Chinese hamster ovary cells. Results obtained are summarized in Table II.

As is seen from data of Table II, compounds of the general Formula I exhibit stronger dose-multiplicative-sensitization than the known reference drugs.

TABLE II

| Test-compound | $D_o$ |
|---|---|
| N—(3-Nitro-4-quinoline)-morpholino-carboxamidine | 1.7 Gy |
| Misonidazole | 2.5 Gy |
| Diamide | 3.3 Gy |
| Untreated controls | 3.75–3.8 Gy |

4. Determination of the quasi threshold dose ($D_q$). These values indicate the minimum dose necessary to the appearance of the end point (cell killing) studied from biological point of view. These results are shown in Table III.

TABLE III

| Test-compound | $D_q$ |
|---|---|
| N—(3-Nitro-4-quinoline)-morpholino-carboxamidine | 0 Gy |
| Misonidazole | 5 Gy |

It is clear from the data of Table III that in case of misonidazole cell killing effect appears only above 5 Gy, while pre-treatment with compounds of the general Formula I leads already to cell lethality following very low dose irradiation.

Gy (gray) is the symbol of the absorbed radiation dose in SI-system. 1 Gy corresponds to the radiation dose when 1 Joule energy is absorbed in 1 kg material exposed to ionizing radiation with constant intensity.

It was also proved in experiments on rodents (mice) that the new compounds of the general Formula I have the advantageous radiosensitizing ability in vivo, too. When administering the new compounds intravenously or per os, the observed long-lasting sensitization showed indirectly the slow metabolization of the molecules and that these compounds exert their effect in unchanged forms. This is important to note because some drugs (mainly the nitrobenzene and nitrofurane), showing beneficial sensitizing properties in bacterial and mammalian cell systems, were almost ineffective in vivo due to the fast degradation in and excretion from the animal organism.

Encouraging results were obtained in experiments with implanted mouse tumor [Lewis lung carcinoma solid tumor, Sugiwara and Stock, Cancer Res. 15, 38 (1955)]. After treatment of the animals with the new compounds of the general Formula I at relatively low concentration (0.2 mM) followed by a local irradiation of 10 Gy, a sensitizing ratio of 1.5-2.1 vas found.

The dose of the compounds of the general Formula I depends on several factors (e.g. the activity of the active ingredient, the state and age of the patient etc.) and is always determined by the prescriptions of the physician. Thus just for the sake of information we mention that the average daily oral dose amounts to from about 0.25 g/m² body surface to about 5.0 g/m² body surface which corresponds to a dose of about 6-120 mg/kg. The above values are, however, only of an approximate nature and the actual dose applied may be lower or higher than the above interval.

According to the present invention there are provided further pharamaceutical compositions comprising at least one compound of the general Formula I in admixture with suitable pharmaceutical carriers.

The said compositions may be in forms suitable for oral or parenteral application. The compositions may be finished in solid (e.g. tablets, drag,ées, pills, coated pills, capsules) or liquid (e.g. solution, suspension or emulsion) form. The pharmaceutical compositions may comprise conventional inert carriers (e.g. talc, calcium carbonate, magnesium carbonate, starch etc.) and also usual excipients and additives (e.g. emulsifying, dispersing, disintegrating agents, buffers, salts modifying osmotic pressure etc.).

The pharmaceutical compositions may be prepared by methods of pharmaceutical industry known per se.

Further details of the present invention are to be found in the following Examples without limiting the scope of protection to the said Examples.

EXAMPLE 1

N-(3-Nitro-4-quinolyl)-morpholino carboxamidine 3.56 g (0.02 mole) of morpholino-carbamidine hemisulfate are heated to boiling with a solution of 0.02 mole of sodium ethylate and 25 ml of ethanol for an hour, whereupon the sodium sulfate formed is filtered off. To the ethanolic solution of the morpholino carbamidine thus obtained 2.09 g (0.01 mole) of 4-chloro-3-nitro-quinoline are added and the orange suspension thus formed is refluxed for 5 hours. The precipitated product is filtered and washed subsequently with water, chloroform and ethanol. After drying 2.62 g of the desired compound are obtained, yield 86%, mp.: 228-230° C. (from ethanol).

Analysis: calculated: C%=55.81; H%=5.04; N%=23.23; found: C%=55.73; H%=5,08; N%=23.19.

The salt of N-(3-nitro-4-quinolyl)-morpholino-carboxamidine formed with an equivalent amount of glyoxylic acid melts at 144°-146° C.; the melting point of the hydrochloride amounts to 252-254° C.

EXAMPLE 2

N-(3-Nitro-4-quinolyl)-N'-tetrahydrofurfuryl-guanidine

A solution of 3.86 g (0.02 mole) of tetrahydrofurfuryl guanidine hemisulfate, 0.02 mole of sodium ethylate and 25 ml of ethanol is refluxed for an hour. To the suspension containing tetrahydrofurfuryl guanidine and sodium sulfate 4.16 g (0.02 mole) of 4-chloro-3-nitro-quinoline are added and the reaction mixture is refluxed for a further hour. The reaction mixture is cooled, the precipitated crystals are filtered, washed subsequently with a saturated sodium hydrogen carbonate solution, water, ethanol and chloroform and dried. Thus 4.44 g of the desired compound are obtained, yield 70.5 %, mp.: 210°-212° C.

Analysis: calculated: C%=57.13; H%=5.43; N%=22.21; found: C%=57.28; H%=5.59; N%=22.30.

EXAMPLES 3-11

One proceeds in an analogous manner to the preceding Examples except that the corresponding starting materials are used. The following compounds are prepared:

3. N-(3-Nitro-4-quinolyl)-4-(2-hydroxyethyl)-piperazinyl-1-carboxamidine

Mp.: 232°-234° C., yield: 91%.

Analysis: calc.: C%=55.80; H%=5.85; N%=24.41; found: C%=56.68; H%=5.99; N%=24.31.

4. N-(3-Nitro-4-quinolyl)-N'-furfuryl-guanidine

Mp.: 210°-212° C., yield: 85%.

Analysis: calc.: C%=57.87; H%=4.21; N%=22.50; found: C%=57.97; H%=4.47; N%=22.31.

5. N-(2-Hydroxyethyl)-N'-(3-nitro-4-quinolyl)-guanidine

Mp.: 228°-230° C., yield: 80%.

Analysis: calc.: C%=52.36; H%=4.76; N%=25.44; found: C%=52.51; H%=4.98; N%=25.12.

6. N-(2-Methoxyethyl)-N'-(3-nitro-4-quinolyl)-guanidine

Mp.: 166°-168° C., yield: 85%.

Analysis: calc.: C%=53.97; H%=5.23; N%=24.21; found: C%=53.79; H%=5.45; N%=24.30.

7. N-(3-Nitro-4-quinolyl)-4-methyl-piperazinyl-1-carboxamidine

Mp.: 249°-250° C., yield: 85%.

Analysis: calc.: C%=57.31; H%=5.77; N%=26.74; found: C%=57.28; H%=5.91; N%=26.50.

8. N-(3-Nitro-4-quinolyl)-piperidino-carboxamidine

Mp.: 248°-251° C., yield: 70%.

Analysis: calc.: C%=60.19; H%=5.73; N%=23.40; found: C%=60.32; H%=5.96; N%=23.26.

9. N-(3-Nitro-4-quinolyl)-3-hydroxy-piperidino-carboxamidine

Mp.: 240°-242° C., yield: 87%.

Analysis: calc.: C%=57.13; H%=5.43; N%=22.21; found: C%=57.30; H%=5.68; N%=22.15.

10. N-(3-Nitro-4-quinolyl)-4-hydroxy-piperidino-carboxamidine

Mp.: 232°-234° C., yield: 88%.

Analysis: calc.: C%=57.13; H%=5.43; N%=22.21; found: C%=57.31; H%=5.51; N%=22.31.

11. N-(7-Chloro-3-nitro-4-quinolyl)-morpholino-carboxamidine

Mp.: 286°-288° C.

Analysis: calc.: C%=50.08; H%=4.20; N%=20.86; Cl%=10.56; found: C%=49.92; H%=4.27; N%=21.06; Cl%=10.22.

What we claim is:

1. Quinoline derivatives of the general Formula I

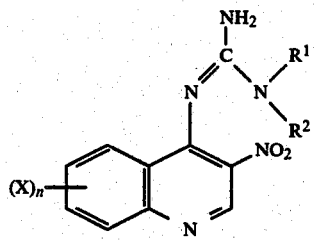

and acid addition salts thereof (wherein
X stands for hydrogen, halogen or lower alkoxy;
n is and integer of 1, 2 or 3;
R$^1$ and R$^2$ together with the adjacent nitrogen atom, they are attached to, form a 5- or 6-membered heterocyclic group which may optionally contain a further oxygen, nitrogen or sulfur heteroatom and may be optionally substituted).

2. Compounds according to claim 1, wherein X is hydrogen.

3. Compounds according to claim 1, wherein R$^1$ and R$^2$ together with the adjacent nitrogen atom, they are attached to, form a morpholino, piperazino, piperidino, 4-(2-hydroxyethyl)-piperazino, 4-hydroxy-piperidino or pyrrolidino group.

4. N-(3-Nitro-4-quinolyl)-morpholino-carboxamidine and acid addition salts thereof.

5. Pharmaceutical compositions comprising as active ingredient at least one compound of the general Formula I (wherein X, n, R$^1$ and R$^2$ are as stated in claim 1) or a pharmaceutically acceptable acid addition salt thereof in admixture with suitable inert pharmaceutical carriers.

6. Pharmaceutical compositions according to claim 5, comprising N-(3-nitro-4-quinolyl)-morpholino-carboxamidine or a pharmaceutically acceptable acid addition salt thereof as active ingredient.

* * * * *